(12) United States Patent
Qi et al.

(10) Patent No.: US 11,585,802 B1
(45) Date of Patent: Feb. 21, 2023

(54) METHOD AND SYSTEM FOR PREDICTING DISTURBANCE RESPONSE TO INJECTION OF CARBON DIOXIDE INTO MULTISCALE ROCK MASS

(71) Applicant: INSTITUTE OF GEOLOGY AND GEOPHYSICS, CAS, Beijing (CN)

(72) Inventors: Shengwen Qi, Beijing (CN); Bowen Zheng, Beijing (CN); Tianming Huang, Beijing (CN); Haijun Zhao, Beijing (CN); Changqian Cao, Beijing (CN); Zhendong Cui, Beijing (CN); Songfeng Guo, Beijing (CN); Xiaolin Huang, Beijing (CN)

(73) Assignee: INSTITUTE OF GEOLOGY AND GEOPHYSICS, CAS, Beijing (CN)

( * ) Notice: Subject to any disclaimer, the term of this patent is extended or adjusted under 35 U.S.C. 154(b) by 0 days.

(21) Appl. No.: 17/940,109

(22) Filed: Sep. 8, 2022

(30) Foreign Application Priority Data

Nov. 11, 2021  (CN) .......................... 202111329545.3

(51) Int. Cl.
  *G01N 33/24* (2006.01)
  *G01N 24/00* (2006.01)
  *G01N 24/08* (2006.01)

(52) U.S. Cl.
  CPC ........... *G01N 33/24* (2013.01); *G01N 24/081* (2013.01)

(58) Field of Classification Search
  CPC ....... G01N 33/24; G01N 24/081; G01D 21/02
  See application file for complete search history.

(56) References Cited

U.S. PATENT DOCUMENTS

| | | | | |
|---|---|---|---|---|
| 2011/0066380 | A1* | 3/2011 | Hager | ..................... E21B 43/16 |
| | | | | 702/12 |
| 2019/0360904 | A1* | 11/2019 | Ju | .......................... E21B 43/164 |
| 2020/0284945 | A1* | 9/2020 | Khan | ...................... G06F 30/20 |

FOREIGN PATENT DOCUMENTS

| | | |
|---|---|---|
| CN | 101458218 B | 2/2011 |
| CN | 106872230 A | 6/2017 |
| CN | 113777278 B | 3/2022 |

OTHER PUBLICATIONS

First office action in corresponding CN 202111329545.3 dated Dec. 24, 2021 (pp. 1-10) and english translation thereof (pp. 1-4).

(Continued)

*Primary Examiner* — Jermele M Hollington
*Assistant Examiner* — Suresh K Rajaputra
(74) *Attorney, Agent, or Firm* — Millen, White, Zelano & Branigan, P.C.; William F. Nixon; Wan Ching

(57) ABSTRACT

The present disclosure relates to a method and system for predicting a disturbance response to an injection of carbon dioxide into a multi-scale rock mass. The method includes: predicting a disturbance response to an injection of supercritical carbon dioxide into a multi-scale rock matrix; predicting a disturbance response to an injection of supercritical carbon dioxide into a multi-scale rock mass structure; and predicting a disturbance response to an injection of supercritical carbon dioxide into a multi-scale rock matrix-rock mass structure system. The method in the present disclosure can accurately analyze a cross-scale spatio-temporal evolution process of the multi-scale rock mass and seepage mechanics under disturbance of the injection of supercritical carbon dioxide.

6 Claims, 1 Drawing Sheet

(56) References Cited

OTHER PUBLICATIONS

Second office action in corresponding CN 202111329545.3 dated Jan. 29, 2022 (pp. 1-5) and english translation thereof (pp. 1-5).
Notice of allowance in corresponding CN 202111329545.3 dated Feb. 24, 2022 (pp. 1-4) and english translation thereof (pp. 1-2).
Xie Jian et al.: "A review of Laboratory Investigation for Mechanism of CO2 capture and Geologic Storage (CCGS)" Advances in New and Renewable Energy; 2016; vol. 4, No. 2; 2095-560X (2016) 02-0132-07 pp. 132-138.
Omer Izgec et al.: "CO2 injection into saline carbonate aquifer formations I: laboratory investigation" Transp Porous Med (2008) 72:1-24, DOI 10.1007/s11242-007-9132-5.
He Kai: "Research on Integrity Evolution and Leakage of CO2 Geological Storage System", A Thesis Submitted to the Northeast Petroleum University Jun. 2019, pp. 1-90.

* cited by examiner

ND SYSTEM FOR PREDICTING
METHOD AND SYSTEM FOR PREDICTING DISTURBANCE RESPONSE TO INJECTION OF CARBON DIOXIDE INTO MULTISCALE ROCK MASS

CROSS REFERENCE TO RELATED APPLICATION

This patent application claims the benefit and priority of Chinese Patent Application No. 202111329545.3, entitled "METHOD AND SYSTEM FOR PREDICTING DISTURBANCE RESPONSE TO INJECTION OF CARBON DIOXIDE INTO MULTI-SCALE ROCK MASS" filed on Nov. 11, 2021, the disclosure of which is incorporated by reference herein in its entirety.

TECHNICAL FIELD

The present disclosure relates to the field of engineering geomechanics of rock mass, in particular, to a method and system for predicting a disturbance response to an injection of carbon dioxide ($CO_2$) into multi-scale rock mass.

BACKGROUND ART

The technological path to reach "peak carbon dioxide emissions" and "carbon neutrality" mainly includes two aspects, namely the reduction in carbon dioxide emissions and increase in carbon sink. At present, the carbon dioxide capture, utilization and storage technology is internationally recognized as the most direct and effective geological carbon sink measurement. The geological carbon dioxide storage technology is to inject industrially captured carbon dioxide in the form of super-critical state (at a temperature higher than 31.1° C., and a pressure higher than 7.38 MPa) into the stratum with appropriate sealing conditions deep underground (at a depth of 800 m or higher) for long-term (scale from thousands to tens of thousands of years) safe seal and isolation. The injection of supercritical carbon dioxide will disturb rock mass in a storage site, resulting in complex chemical, physical and mechanical responses. Quantitative prediction on the disturbance response of multi-scale rock mass to the injection of supercritical carbon dioxide is the key to scientifically and reasonably select a storage site.

Rock mass is a geological body with multi-scale structural characteristics, which is composed of rock matrix and rift cracks. Rock matrix and fracture fissures jointly determine the physical, mechanical and seepage characteristics of rock mass. Regarding rock matrix, people have grasped, from the aspects of chemistry, physics and mechanics, certain knowledge about the change law of porosity and permeability of rock matrix under the injection of supercritical carbon dioxide. However, there is lack of study on integration of geochemical reaction and physical mechanics, making it difficult to accurately predict the dynamic changes of porosity, permeability and seepage mechanics parameters of the rock matrix under the disturbance of supercritical carbon dioxide injection. There is a lack of large-scale physical simulation experiments regarding fracture fissures, and the research results of a single fracture are not sufficient to reflect the law of response of complex fracture networks in rock mass to the injection of supercritical carbon dioxide. At the same time, traditional laboratory tests can hardly achieve real-time visual tracking on the process of multi-scale fracture evolution and gas-liquid migration in rock mass.

On the premise of fine description of multi-scale rock mass, the present disclosure provides a test method suitable for predicting the disturbance response to the injection of supercritical carbon dioxide into multi-scale rock mass at the storage sites for carbon dioxide, which accurately analyzes the cross-scale spatial-temporal evolution process of multi-scale rock mass and seepage mechanics under disturbance of supercritical carbon dioxide injection, thereby meeting the current requirements for geological storage potential of carbon dioxide and suitability evaluation.

SUMMARY

An objective of the present disclosure is to provide a method and system for predicting a disturbance response to an injection of carbon dioxide into a multi-scale rock mass, so as to accurately analyze the cross-scale spatio-temporal evolution process of the multi-scale rock mass and seepage mechanics under disturbance of supercritical carbon dioxide injection.

In order to achieve the above objective, the present disclosure provides the following technical solutions.

The present disclosure provides a method for predicting a disturbance response to an injection of carbon dioxide into a multi-scale rock mass, including:

predicting a disturbance response to an injection of supercritical carbon dioxide into a multi-scale rock matrix, where predicting the disturbance response to the injection of supercritical carbon dioxide into the multi-scale rock matrix comprises conducting a chemical response prediction on the multi-scale rock matrix under conditions of different pressures, different temperatures and different injection scenarios; and conducting a physical and mechanical response prediction on the multi-scale rock matrix under conditions of different pressures, different temperatures and different injection scenarios;

predicting a disturbance response to an injection of supercritical carbon dioxide into a multi-scale rock mass structure, where predicting the disturbance response to the injection of supercritical carbon dioxide into the multi-scale rock mass structure comprises predicting a disturbance response to an injection of carbon dioxide into a rock mass structure in a test sample scale, and predicting a disturbance response to the injection of carbon dioxide into the rock mass structure in a physical model scale; and predicting a disturbance response to an injection of supercritical carbon dioxide into a multi-scale rock matrix-rock mass structure system.

Optionally, conducting the chemical response prediction on the multi-scale rock matrix under conditions of different pressures, different temperatures and different injection scenarios specifically includes:

acquiring typical rocks respectively from a deep saline aquifer, a depleted oil and gas reservoir and a deep un-minable coal seam, and processing the typical rocks into specimens;

injecting supercritical carbon dioxide into each specimen using a nuclear magnetic resonance (NMR) core displacement device;

simulating, by orthogonal experimentation, working conditions of different stresses, different temperatures and different injection scenarios using a loading system and a temperature control system of the NMR core displacement device to monitor in real time a spatio-temporal response process of changes of fluidic chemical compositions and isotope compositions of the rocks;

processing samples before and after a displacement test to samples suitable for microscopic-nanoscopic test imaging;

conducting test imaging on the processed samples in a micro-nano scale by using a scanning electron microscope; and comparing similarities and differences of the fluidic chemical compositions and the isotope compositions of the rocks before and after the displacement test.

Optionally, conducting the physical and mechanical response prediction on the multi-scale rock matrix under conditions of different injection scenarios specifically includes:

acquiring typical rocks respectively from the deep saline aquifer, the depleted oil and gas reservoir and the deep un-minable coal seam, and processing the typical rocks into specimens;

processing the specimen to form a non-penetrating injection hole on an end face of the specimen along a central axis;

injecting supercritical carbon dioxide into the injection hole, simulating working conditions of different stresses, different temperatures and different injection times by orthogonal experimentation using a Computed Tomography (CT) scanning rock multi-field coupling mechanics test system in combination with an acoustic emission system, and monitoring in real time, from macroscale to microscale, a spatio-temporal response process of changes of material compositions and pore structure of the rock matrix through a CT scanning device of the CT scanning rock multi-field coupling mechanics test system; and monitoring in real time, by an infrared thermometer, a spatio-temporal response process of changes of parameters of a rock temperature field; monitoring in real time, by a seepage field monitor, a spatio-temporal response process of changes of parameters of a rock seepage field; and monitoring in real time, by a hydraulic sensor, a spatio-temporal response process of changes of initiation pressure and fracture pressure of the rocks during the injection of carbon dioxide.

Optionally, predicting the disturbance response to the injection of carbon dioxide into the rock mass structure in the test sample scale specifically includes:

acquiring typical rocks respectively from the deep saline aquifer, the depleted oil and gas reservoir and the deep un-minable coal seam, and processing the typical rocks to specimens containing artificial fractures;

processing each specimen to form a non-penetrating injection hole on an end face of the specimen along a central axis;

injecting supercritical carbon dioxide mingled with magnetic Fe nanoparticles into the injection hole; simulating, by orthogonal experimentation using a CT scanning rock multi-field coupling mechanics test system in combination with an acoustic emission system, working conditions of different stresses, different temperatures, different injection times, different fracture surface roughness, different fracture surface bonding strengths, and different included angles between an axis of the injection hole and fracture surfaces, and monitoring in real time, in test sample scale, an activation fracture process of the fracture surfaces;

monitoring in real time pumping pressure, temperature and flow indicators using the CT scanning rock multi-field coupling mechanics test system;

monitoring in real time pressure, axial displacement and radial displacement of the specimens using a high-precision force and displacement sensor;

measuring, by a nuclear magnetic resonance apparatus, distributions of magnetic Fe nanoparticles on the fracture surfaces under different working conditions, and determining activation dislocation regions of the fracture surfaces;

conducting scanning and three-dimensional reconstruction on morphology of the fracture surfaces before and after a test by using a three-dimensional laser scanner to obtain three-dimensional morphology parameters of the fracture surfaces, and comparing similarities and differences of the three-dimensional morphology parameters of the fracture surfaces before and after the test; and during the test, monitoring in real time a spatio-temporal response process of changes of chemical compositions of rock mineral and aqueous solution on the fracture surfaces, and obtaining fracture surface roughness, degree of opening, temperature, seepage, stress, deformation and chemical parameters of different supercritical carbon dioxide injection parameters.

Optionally, predicting the disturbance response to the injection of carbon dioxide into the rock mass structure in physical model scale specifically includes:

for the deep saline aquifer, the depleted oil and gas reservoir and the deep un-minable coal seam, generalizing, with a typical three-dimensional rock mass structure featuring reservoir, caprock and overlying strata taken into consideration, a scaled physical model which can reflect characteristics of main rock mass structures;

constructing, by photosensitive materials and 3D printing technology, a plurality of photosensitive material rock mass elements with a fracture network;

stacking the photosensitive material rock mass elements, bonding the photosensitive material rock mass elements into a large-sized rock mass physical model, and processing the large-sized rock mass physical model to form a non-penetrating injection hole, where the injection hole passes through the overlying strata and caprock to reach the reservoir;

applying a preset temperature and stress to a boundary of the physical model until an equilibrium is reached, and injecting supercritical carbon dioxide mingled with a fluorescent agent into the injection hole;

monitoring in real time a spatio-temporal response process of temperature in a fracture network model by an infrared measuring instrument;

monitoring in real time a spatio-temporal response process of seepage flow in the fracture network model by using a fluid fluoroanalyzer;

monitoring in real time a spatio-temporal response process of stress in the fracture network model by using a photoelastic test; and monitoring in real time, by a digital image method, a spatio-temporal response process of displacement in the fracture network model, obtaining parameters of a temperature field, a seepage field, a stress field and a displacement field in the fracture network model, quantitatively tracking an evolution process of fracture initiation, extension and penetration in real time, and monitoring dynamic changes of structure parameters, deformation strength parameters and seepage mechanics parameters of rock mass.

Optionally, predicting the disturbance response to the injection of supercritical carbon dioxide into the multi-scale rock matrix-rock mass structure system specifically includes:

for the deep saline aquifer, the depleted oil and gas reservoir and the deep un-minable coal seam, building a multi-field coupling numerical simulation model of the multi-scale rock matrix-rock mass structure system integrating reservoir, caprock and overlying strata;

based on disturbance response data regarding the injection of supercritical carbon dioxide into the multi-scale rock matrix and the multi-scale rock mass structure, simulating, by orthogonal numerical experimentation, a cross-scale spatio-temporal response process of the rock matrix-rock mass structure system integrating reservoir and caprock in nano-micro-meso scale, specimen scale, physical model scale, and engineering scale after injecting carbon dioxide; and according to a change law of mutual feedback among carbon dioxide injection parameters and chemical, physical and mechanical parameters of the reservoir-caprock rock matrix, monitoring in real time an expansion change of the reservoir-caprock rock mass structure and migration and distribution of carbon dioxide, and obtaining parameters of a chemical field, a temperature field, a seepage field and a stress field of the multi-scale rock matrix-rock mass structure system integrating reservoir and caprock with different carbon dioxide injection parameters.

Based on the above method, the present disclosure further provides a system for predicting the disturbance response to the injection of carbon dioxide into the multi-scale rock mass, including:

a first response prediction module configured to predict a disturbance response to an injection of supercritical carbon dioxide into a multi-scale rock matrix by conducting a chemical response prediction on the multi-scale rock matrix under conditions of different pressures, different temperatures and different injection scenarios; and conducting a and physical and mechanical response prediction on the multi-scale rock matrix under conditions of different pressures, different temperatures and different injection scenarios;

a second response prediction module configured to predict a disturbance response to an injection of supercritical carbon dioxide into a multi-scale rock mass structure by predicting a disturbance response to an injection of carbon dioxide into a rock mass structure in test sample scale, and predicting a disturbance response to the injection of carbon dioxide into the rock mass structure in physical model scale; and a third response prediction module configured to predict a disturbance response to an injection of supercritical carbon dioxide into a multi-scale rock matrix-rock mass structure system.

According to the specific embodiments provided by the present disclosure, the present disclosure discloses the following technical effects:

The foregoing method of the present disclosure conducts, based on the proven multi-scale (macroscale, mesoscale, microscale, nanoscale) and multi-field (chemical field, temperature field, seepage field, stress field) coupling laboratory experiment and numerical simulation in combination with transparent rock mass model of 3D printing technology, physical simulation under complex geological conditions, and can realize quantitative analysis of the disturbance response to the injection of carbon dioxide into multi-scale rock mass at the storage site. In this way, a foundation is laid for establishing a dynamic prediction model of physical property change, fracture evolution and gas-liquid migration of multi-scale rock mass at the storage site under disturbance of carbon dioxide injection.

BRIEF DESCRIPTION OF THE DRAWINGS

To describe the embodiments of the present disclosure or the technical solutions in the related art more clearly, the accompanying drawings required in the embodiments are briefly introduced below. Obviously, the accompanying drawings described below are only some embodiments of the present disclosure. A person of ordinary skill in the art may further obtain other accompanying drawings based on these accompanying drawings without any creative effort.

DETAILED DESCRIPTION OF THE EMBODIMENTS

The technical solutions of the embodiments of the present disclosure are clearly and completely described below with reference to the accompanying drawings. Apparently, the described embodiments are merely a part rather than all of the embodiments of the present disclosure. All other embodiments obtained by those of ordinary skill in the art based on the embodiments of the present disclosure without creative efforts shall fall within the protection scope of the present disclosure.

An objective of the present disclosure is to provide a method and system for predicting a disturbance response to an injection of carbon dioxide into multi-scale rock mass, so as to accurately analyze the cross-scale spatio-temporal evolution process of multi-scale rock mass and seepage mechanics under disturbance of the injection of supercritical carbon dioxide.

To make the above-mentioned objective, features, and advantages of the present disclosure clearer and more comprehensible, the present disclosure will be further described in detail below in conjunction with the accompanying drawings and specific embodiments.

Figure 1:
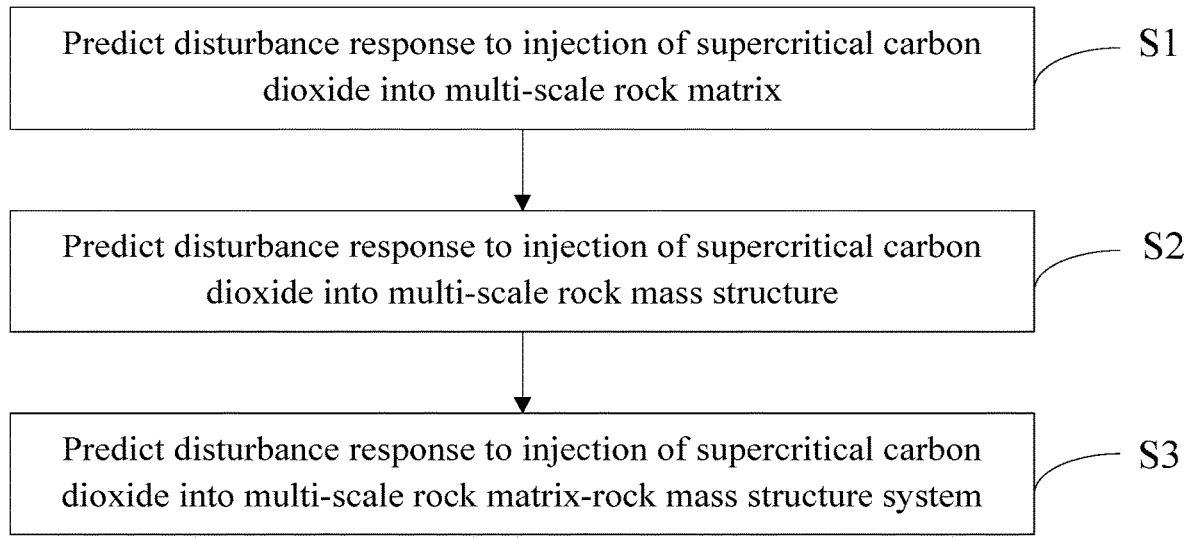
FIG. 1 is a flowchart of a method for predicting a disturbance response to an injection of carbon dioxide into multi-scale rock mass according to an embodiment of the present disclosure.

FIG. 1 is a flowchart of a method for predicting a disturbance response to an injection of carbon dioxide into multi-scale rock mass according to an embodiment of the present disclosure. As shown in FIG. 1, the method includes steps S1-S3.

Step S1: a disturbance response to an injection of supercritical carbon dioxide into a multi-scale rock matrix is predicted, where predicting the disturbance response to the injection of supercritical carbon dioxide into the multi-scale rock matrix, comprises conducting a chemical response prediction and a physical and mechanical response prediction on the multi-scale rock matrix under conditions of different pressures, different temperatures and different injection scenarios.

Specifically, the step of conducting the chemical response prediction on the multi-scale rock matrix under conditions of different pressures, different temperatures and different injection scenarios, includes:

step 101: acquiring typical rocks respectively from a deep saline aquifer, a depleted oil and gas reservoir and a deep un-minable coal seam, and processing the typical rocks to form cylindrical specimens;

step 102: injecting supercritical carbon dioxide into the specimens in a core clamp holder of a nuclear magnetic resonance (NMR) core displacement device using the NMR core displacement device; simulating, by the way of orthogonal experimentation using a loading system and a temperature control system of the NMR core displacement device, working conditions of different stresses (stress values greater than 7.38 MPa, such as 10 MPa, 20 MPa, 30 MPa, 40 MPa, or 50 MPa), different temperatures (temperature values greater than 31.1° C., such as 35° C., 45° C., 55° C., 65° C., 75° C., 85° C. or 95° C.) and different injection scenarios (e.g., injection of $CO_2$, alternate injection of $CO_2$ and water, injection of saturated $CO_2$ solution, etc.); and monitoring in real time a spatio-temporal response process of changes of parameters of fluidic chemical compositions and isotope compositions of the rocks in macroscale-microscale; and step 103: processing the specimens before and after a displacement test to samples suitable for microscopic-nanoscopic test imaging; conducting the test imaging in a micro-nano scale by using a scanning electron microscope; and comparing the parameters of the fluidic chemical composition and isotope composition of the rocks before and after the displacement test.

The step of conducting the physical and mechanical response prediction on the multi-scale rock matrix under conditions of different injection scenarios, specifically includes:

step 201: acquiring the typical rocks respectively from the deep saline aquifer, the depleted oil and gas reservoir and the deep un-minable coal seam; processing the typical rocks to the cylindrical specimens; and processing each specimen to form a non-penetrating injection hole on an end face of the specimen along a central axis;

step 202: injecting supercritical carbon dioxide into the injection hole; simulating, by the way of orthogonal experimentation using a CT scanning rock multi-field coupling mechanics test system in combination with an acoustic emission system, working conditions such as different stresses (stress values greater than 7.38 MPa, such as 10 MPa, 20 MPa, 30 MPa, 40 MPa, and 50 MPa), different temperatures (temperature values greater than 31.1° C., such as 35° C., 45° C., 55° C., 65° C., 75° C., 85° C., and 95° C.) and different injection times (exceeding 0.1 h, such as 0.5 h, 1 h, 6 h, 12 h, and 24 h); and monitoring in real time, from a macroscale to a microscale, a spatio-temporal response process of changes of structure field parameters such as material composition and pore structure of the rock matrix through a CT scanning device of the rock multi-field coupling mechanics test system; and step 203: monitoring in real time, via an infrared thermometer, a spatio-temporal response process of changes of parameters of a temperature field of the rocks; monitoring in real time, via a seepage field monitor, a spatio-temporal response process of changes of parameters of a seepage field of the rocks; and monitoring in real time, via a hydraulic sensor, a spatio-temporal response process of changes of stress field parameters such as initiation pressure and fracture pressure of the rocks during the injection of carbon dioxide.

Step S2: a disturbance response to the injection of carbon dioxide into a multi-scale rock mass structure is predicted, which comprises predicting a disturbance response to the injection of carbon dioxide into the rock mass structure in test sample scale, and predicting a disturbance response to the injection of carbon dioxide into the rock mass structure in physical model scale.

Specifically, the step of predicting the disturbance response to the injection of carbon dioxide into the rock mass structure in test sample scale specifically includes:

step 301: acquiring typical rocks respectively from the deep saline aquifer, the depleted oil and gas reservoir and the deep un-minable coal seam; processing the typical rocks to form cylindrical specimens containing artificial fractures; and processing each cylindrical specimen to form a non-penetrating injection hole on an end face of the specimen along a central axis;

step 302: injecting supercritical carbon dioxide mingled with magnetic Fe nanoparticles into the injection hole; simulating, by the way of orthogonal experimentation using the CT scanning rock multi-field coupling mechanics test system in combination with the acoustic emission system, working conditions of different stresses (stress values greater than 7.38 MPa, such as 10 MPa, 20 MPa, 30 MPa, 40 MPa and 50 MPa), different temperatures (temperature values greater than 31.1° C., such as 35° C., 45° C., 55° C., 65° C., 75° C., 85° C. and 95° C.), different injection times (time values greater than 0.1 h, such as 0.5 h, 1 h, 6 h, 12 h and 24 h), different fracture surface roughness, different fracture surface bonding strengths, and different included angles (e.g., 0°, 15°, 30°, 45°, 60°, 75° and 90°) between an axis of the injection hole and a fracture surface; and monitoring in real time, in test sample scale, an activation fracture process of the fracture surface; and step 303: monitoring in real time pumping pressure, temperature and flow indicators using the CT scanning rock multi-field coupling mechanics test system, and monitoring in real time pressure, axial displacement and radial displacement of the specimens via a high-precision force and displacement sensor; measuring distribution of magnetic Fe nanoparticles on the fracture surfaces under different working conditions and determining activation dislocation regions of the fracture surfaces using a nuclear magnetic resonance apparatus; conducting scanning and three-dimensional reconstruction on morphology of the fracture surfaces before and after a test by using a three-dimensional laser scanner to obtain three-dimensional morphology parameters of the fracture surfaces, and comparing similarities and differences of the three-dimensional morphology parameters of the fracture surfaces before and after the test; and during the test, monitoring in real time a spatio-temporal response process of changes of parameters of chemical compositions of rock mineral and aqueous solution on the fracture surfaces, and obtaining parameters such as fracture surface roughness, degree of opening, temperature, seepage, stress, deformation, and chemistry under the conditions of different supercritical carbon dioxide injection parameters.

The step of predicting the disturbance response to the injection of carbon dioxide into the rock mass structure in physical model scale, specifically includes:

for the deep saline aquifer, the depleted oil and gas reservoir, and the deep un-minable coal seam, considering a typical three-dimensional rock mass structure including reservoir-caprock-overlying strata, and performing a similarity theory analysis to generalize a scaled physical model which can reflect characteristics of the main rock mass structure (reservoir-caprock-overlying strata); constructing a plurality of photosensitive material rock mass elements with a fracture network by using the photosensitive materials and 3D printing technology; stacking the photosensitive material rock mass elements and bond the stacked photosensitive material rock mass elements into a large-sized rock mass physical model, and processing the large-sized rock mass physical model to form a non-penetrating injection hole, where the injection hole passes through the overlying strata and caprock to reach the reservoir; and applying a preset temperature and stress to a boundary of the physical model until an equilibrium is reached, and injecting supercritical carbon dioxide mingled with a fluorescent agent into the injection hole, so as to conduct a research on a spatio-temporal response of the rock mass structure and seepage characteristics under the condition of multi-field coupling, where during the test, a spatio-temporal response process of temperature in a fracture network model is monitored in real time by using an infrared measurement technology; a spatio-temporal response process of seepage flow in the fracture network model is monitored in real time by using a fluid fluoroanalyzer; a spatio-temporal response process of stress in the fracture network model is monitored in real time by using a photoelastic test; a spatio-temporal response process of displacement in the fracture network model is monitored in real time with the aid of digital imaging and other related techniques; and parameters of a temperature field, a seepage field, a stress field and a displacement field in the fracture network model are obtained, an evolution process of fracture initiation, extension and penetration is quantitatively tracked in real time, and dynamic changes of structure parameters, deformation strength parameters and seepage mechanics parameters of the rock mass are monitored.

Step S3: a disturbance response to the injection of supercritical carbon dioxide into a multi-scale rock matrix-rock mass structure system is predicted.

For the deep saline aquifer, the depleted oil and gas reservoir, and the deep un-minable coal seam, a multi-field coupling numerical simulation model of the multi-scale rock matrix-rock mass structure (pore-fissure-fracture) system integrating reservoir, caprock and overlying strata, is built respectively, so as to conduct a research on a spatio-temporal response law of the multi-scale rock mass at a storage site under disturbance of the injection of supercritical carbon dioxide. Based on the obtained disturbance response data regarding the injection of supercritical carbon dioxide into the multi-scale rock matrix and the multi-scale rock mass structure, by the way of orthogonal numerical experimentation, a cross-scale spatio-temporal response process of the system of reservoir-caprock rock matrix-rock mass structure (pore-fissure-fracture) after injecting carbon dioxide in scales such as a nano-micro-meso scale, a specimen scale, a physical model scale, and an engineering scale, is simulated. A change law of mutual feedback among carbon dioxide injection parameters and chemical, physical and mechanical parameters of the reservoir-caprock rock matrix is studied. An expansion change of the reservoir-caprock rock mass structure (pore-fissure-fracture) and migration and distribution of carbon dioxide, are monitored in real time. Parameters of a chemical field, a temperature field, a seepage field and a stress field of the multi-scale rock matrix-rock mass structure (pore-fissure-fracture) system integrating reservoir and caprock with different carbon dioxide injection parameters, are obtained.

Figure 2:
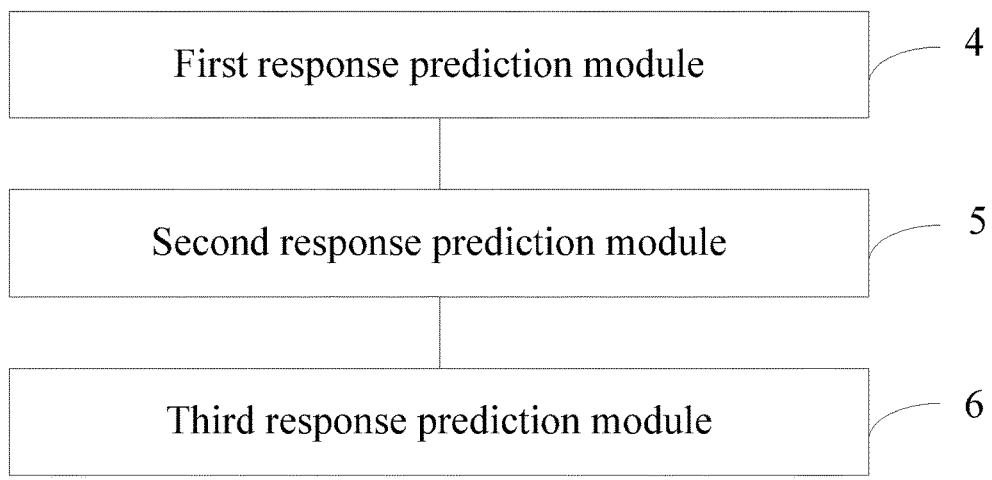
FIG. 2 is a schematic structural diagram of a system for predicting the disturbance response to the injection of carbon dioxide into multi-scale rock mass according to an embodiment of the present disclosure.

FIG. 2 is a schematic structural diagram of a system for predicting a disturbance response to an injection of carbon dioxide into multi-scale rock mass according to an embodiment of the present disclosure. As shown in FIG. 2, the system includes:

a first response prediction module 4 configured to predict a disturbance response to an injection of supercritical carbon dioxide into a multi-scale rock matrix by conducting a chemical response prediction and a physical and mechanical response prediction on the multi-scale rock matrix under conditions of different pressures, different temperatures and different injection scenarios;

a second response prediction module 5 configured to predict a disturbance response to an injection of supercritical carbon dioxide into a multi-scale rock mass structure by predicting a disturbance response to the injection of carbon dioxide into the rock mass structure in test sample scale, and predicting a disturbance response to the injection of carbon dioxide into the rock mass structure in physical model scale; and a third response prediction module 6 configured to predict a disturbance response to an injection of supercritical carbon dioxide into a multi-scale rock matrix-rock mass structure system.

Each example of the present specification is described in a progressive manner, each example focuses on the difference from other examples, and the same and similar parts between the examples may refer to each other. Since the system disclosed in an embodiment corresponds to the method disclosed in another embodiment, the description is relatively simple, and reference can be made to the method description.

Specific examples are used herein to explain the principles and embodiments of the present disclosure. The foregoing description of the embodiments is merely intended to help understand the method of the present disclosure and its core ideas; besides, various modifications may be made by a person of ordinary skill in the art to specific embodiments and the scope of application in accordance with the ideas of the present disclosure. In conclusion, the content of the present description shall not be construed as limitations to the present disclosure.

What is claimed is:

1. A method for predicting a disturbance response to an injection of carbon dioxide into a multi-scale rock mass, comprising:

predicting a disturbance response to an injection of supercritical carbon dioxide into a multi-scale rock matrix, wherein predicting the disturbance response to the injection of supercritical carbon dioxide into the multi-scale rock matrix comprises conducting a chemical response prediction on the multi-scale rock matrix under conditions of different pressures, different temperatures and different injection scenarios; and conducting a physical and mechanical response prediction on the multi-scale rock matrix under conditions of different pressures, different temperatures and different injection scenarios;

predicting a disturbance response to an injection of supercritical carbon dioxide into a multi-scale rock mass structure, wherein predicting the disturbance response to the injection of supercritical carbon dioxide into the multi-scale rock mass structure comprises predicting a disturbance response to an injection of carbon dioxide into a rock mass structure in a test sample scale, and predicting a disturbance response to the injection of carbon dioxide into the rock mass structure in a physical model scale; and predicting a disturbance response to an injection of supercritical carbon dioxide into a multi-scale rock matrix-rock mass structure system, wherein predicting the disturbance response to the injection of carbon dioxide into the rock mass structure in the physical model scale comprises:

for a deep saline aquifer, a depleted oil and gas reservoir and a deep un-minable coal seam, generalizing, with a typical three-dimensional rock mass structure integrating reservoir, caprock and overlying strata taken into consideration, a scaled physical model which can reflect characteristics of main rock mass structures;

constructing, by photosensitive materials and 3D printing technology, a plurality of photosensitive material rock mass elements with a fracture network;

stacking the photosensitive material rock mass elements, bonding the photosensitive material rock mass elements into a large-sized rock mass physical model, and processing the large-sized rock mass physical model to form a non-penetrating injection hole, wherein the injection hole passes through the overlying strata and caprock to reach the reservoir;

applying a preset temperature and stress to a boundary of the physical model until an equilibrium is reached, and injecting supercritical carbon dioxide mingled with a fluorescent agent into the injection hole;

monitoring in real time a spatio-temporal response process of temperature in a fracture network model by an infrared measuring instrument;

monitoring in real time a spatio-temporal response process of seepage flow in the fracture network model by using a fluid fluoroanalyzer;

monitoring in real time a spatio-temporal response process of stress in the fracture network model by using a photoelastic test; and monitoring in real time, by a digital image method, a spatio-temporal response process of displacement in the fracture network model, obtaining parameters of a temperature field, a seepage field, a stress field and a displacement field in the fracture network model, quantitatively tracking an evolution process of fracture initiation, extension and penetration in real time, and monitoring dynamic changes of structure parameters, deformation strength parameters and seepage mechanics parameters of rock mass.

2. The method for predicting the disturbance response to the injection of carbon dioxide into the multi-scale rock mass according to claim 1, wherein conducting the chemical response prediction on the multi-scale rock matrix under conditions of different pressures, different temperatures and different injection scenarios comprises:

acquiring typical rocks respectively from a deep saline aquifer, a depleted oil and gas reservoir and a deep un-minable coal seam, and processing the typical rocks into specimens;

injecting supercritical carbon dioxide into each specimen using a nuclear magnetic resonance (NMR) core displacement device;

simulating, by orthogonal experimentation, working conditions of different stresses, different temperatures and different injection scenarios using a loading system and a temperature control system of the NMR core displacement device to monitor in real time a spatio-temporal response process of changes of fluidic chemical compositions and isotope compositions of the rocks;

processing samples before and after a displacement test to samples suitable for microscopic-nanoscopic test imaging;

conducting test imaging on the processed samples in a micro-nano scale by using a scanning electron microscope; and comparing similarities and differences of the fluidic chemical compositions and the isotope compositions of the rocks before and after the displacement test.

3. The method for predicting the disturbance response to the injection of carbon dioxide into the multi-scale rock mass according to claim 1, wherein conducting the physical and mechanical response prediction on the multi-scale rock matrix under conditions of different injection scenarios comprises:

acquiring typical rocks respectively from a deep saline aquifer, a depleted oil and gas reservoir and a deep un-minable coal seam, and processing the typical rocks into specimens;

processing the specimen to form a non-penetrating injection hole on an end face of the specimen along a central axis;

injecting supercritical carbon dioxide into the injection hole, simulating working conditions of different stresses, different temperatures and different injection times by orthogonal experimentation using a Computed Tomography (CT) scanning rock multi-field coupling mechanics test system in combination with an acoustic emission system, and monitoring in real time, from a macroscale to a microscale, a spatio-temporal response process of changes of material compositions and pore structure of the rock matrix through a CT scanning device of the CT scanning rock multi-field coupling mechanics test system; and monitoring in real time, by an infrared thermometer, a spatio-temporal response process of changes of parameters of a rock temperature field; monitoring in real time, by a seepage field monitor, a spatio-temporal response process of changes of parameters of a rock seepage field; and monitoring in real time, by a hydraulic sensor, a spatio-temporal response process of changes of initiation pressure and fracture pressure of the rocks during the injection of carbon dioxide.

4. The method for predicting the disturbance response to the injection of carbon dioxide into the multi-scale rock mass according to claim 1, wherein predicting the disturbance response to the injection of carbon dioxide into the rock mass structure in the test sample scale comprises:

acquiring typical rocks respectively from a deep saline aquifer, a depleted oil and gas reservoir and a deep un-minable coal seam, and processing the typical rocks to specimens containing artificial fractures;

processing the specimen to form a non-penetrating injection hole on an end face of the specimen along a central axis;

injecting supercritical carbon dioxide mingled with magnetic Fe nanoparticles into the injection hole; simulating, by orthogonal experimentation using a CT scanning rock multi-field coupling mechanics test system in combination with an acoustic emission system, working conditions of different stresses, different temperatures, different injection times, different fracture surface roughness, different fracture surface bonding strengths, and different included angles between an axis of the injection hole and fracture surfaces; and monitoring in real time, in test sample scale, an activation fracture process of the fracture surfaces;

monitoring in real time pumping pressure, temperature and flow indicators using the CT scanning rock multi-field coupling mechanics test system;

monitoring in real time pressure, axial displacement and radial displacement of the specimens using a high-precision force and displacement sensor;

measuring, by a nuclear magnetic resonance apparatus, distributions of magnetic Fe nanoparticles on the fracture surfaces under different working conditions, and determining activation dislocation regions of the fracture surfaces;

conducting scanning and three-dimensional reconstruction on morphology of the fracture surfaces before and after a test by using a three-dimensional laser scanner to obtain three-dimensional morphology parameters of the fracture surfaces, and comparing similarities and differences of the three-dimensional morphology parameters of the fracture surfaces before and after the test; and during the test, monitoring in real time a spatio-temporal response process of changes of chemical compositions of rock mineral and aqueous solution on the fracture surfaces, and obtaining fracture surface roughness, degree of opening, temperature, seepage, stress, deformation and chemical parameters of different supercritical carbon dioxide injection parameters.

5. The method for predicting the disturbance response to the injection of carbon dioxide into the multi-scale rock mass according to claim 1, wherein predicting the disturbance response to the injection of supercritical carbon dioxide into the multi-scale rock matrix-rock mass structure system comprises:

for a deep saline aquifer, a depleted oil and gas reservoir and a deep un-minable coal seam, building a multi-field coupling numerical simulation model of the multi-scale rock matrix-rock mass structure system integrating reservoir, caprock and overlying strata;

based on disturbance response data regarding the injection of supercritical carbon dioxide into the multi-scale rock matrix and the multi-scale rock mass structure, simulating, by orthogonal numerical experimentation, a cross-scale spatio-temporal response process of the rock matrix-rock mass structure system integrating reservoir and caprock in a nano-micro-meso scale, a specimen scale, a physical model scale, and an engineering scale after injecting carbon dioxide; and according to a change law of mutual feedback among carbon dioxide injection parameters and chemical, physical and mechanical parameters of the reservoir-caprock rock matrix, monitoring in real time an expansion change of the reservoir-caprock rock mass structure and migration and distribution of carbon dioxide, and obtaining parameters of a chemical field, a temperature field, a seepage field and a stress field of the multi-scale rock matrix-rock mass structure system integrating reservoir and caprock with different carbon dioxide injection parameters.

6. A system for predicting a disturbance response to an injection of carbon dioxide into a multi-scale rock mass, comprising:

a first response prediction module configured to predict a disturbance response to an injection of supercritical carbon dioxide into a multi-scale rock matrix by conducting a chemical response prediction on the multi-scale rock matrix under conditions of different pressures, different temperatures and different injection scenarios; and conducting a physical and mechanical response prediction on the multi-scale rock matrix under conditions of different pressures, different temperatures and different injection scenarios;

a second response prediction module configured to predict a disturbance response to an injection of supercritical carbon dioxide into a multi-scale rock mass structure by predicting a disturbance response to an injection of carbon dioxide into a rock mass structure in a test sample scale, and predicting a disturbance response to the injection of carbon dioxide into the rock mass structure in a physical model scale, wherein predicting the disturbance response to the injection of carbon dioxide into the rock mass structure in the physical model scale comprises:

for a deep saline aquifer, a depleted oil and gas reservoir and a deep un-minable coal seam, generalizing, with a typical three-dimensional rock mass structure integrating reservoir, caprock and overlying strata taken into consideration, a scaled physical model which can reflect characteristics of main rock mass structures;

constructing, by photosensitive materials and 3D printing technology, a plurality of photosensitive material rock mass elements with a fracture network;

stacking the photosensitive material rock mass elements, bonding the photosensitive material rock mass elements into a large-sized rock mass physical model, and processing the large-sized rock mass physical model to form a non-penetrating injection hole, wherein the injection hole passes through the overlying strata and caprock to reach the reservoir;

applying a preset temperature and stress to a boundary of the physical model until an equilibrium is reached, and injecting supercritical carbon dioxide mingled with a fluorescent agent into the injection hole;

monitoring in real time a spatio-temporal response process of temperature in a fracture network model by an infrared measuring instrument;

monitoring in real time a spatio-temporal response process of seepage flow in the fracture network model by using a fluid fluoroanalyzer;

monitoring in real time a spatio-temporal response process of stress in the fracture network model by using a photoelastic test; and monitoring in real time, by a digital image method, a spatio-temporal response process of displacement in the fracture network model, obtaining parameters of a temperature field, a seepage field, a stress field and a displacement field in the fracture network model, quantitatively tracking an evolution process of fracture initiation, extension and penetration in real time, and monitoring dynamic changes of structure parameters, deformation strength parameters and seepage mechanics parameters of rock mass; and a third response prediction module configured to predict a disturbance response to an injection of supercritical carbon dioxide into a multi-scale rock matrix-rock mass structure system.

* * * * *